United States Patent [19]
Alink et al.

[11] 3,959,313
[45] May 25, 1976

[54] PREPARATION OF DITHIOLIUM COMPOUNDS

[75] Inventors: Bernardus A. Oude Alink, St. Louis; Derek Redmore, Ballwin, both of Mo.

[73] Assignee: Petrolite Corporation, St. Louis, Mo.

[22] Filed: May 20, 1974

[21] Appl. No.: 471,285

[52] U.S. Cl. ............................. 260/327 C; 252/395
[51] Int. Cl.² ....................................... C07D 339/04
[58] Field of Search ............................... 260/327 C

[56] References Cited
UNITED STATES PATENTS
3,186,995    6/1965    Klingsberg ...................... 260/294.8

OTHER PUBLICATIONS
Klingsberg, et al., C.A. 57: pp. 16791–16792, (1962).
Klingsberg, J.A.C.S. 83: No. 13, pp. 2934–2937, (1961).
Gaudin et al., Compt. Rend., Vol. 224, pp. 577 to 578 (1947).
Breslow et al., Multi–Sulfur and Sulfur and Oxygen Five– and Six–Membered Heterocycles, Part One, pp. 385 and 397–398, Interscience Publishers, John Wiley and Sons, (1966).

*Primary Examiner*—John D. Randolph
*Attorney, Agent, or Firm*—Sidney B. Ring; Hyman F. Glass

[57] ABSTRACT

This invention relates to the oxidation of sterically hindered 1,2-dithiole-3-thiones with nitric acid to form the corresponding 1,2-dithiolium compounds. For example, when 4-neopentyl-5-tert-butyl-1,2-dithiole-3-thione is oxidized with nitric acid, 4-neopentyl 5-tert-butyl 1,2-dithiolium hydrogen sulfate is formed. When non-sterically hindered 1,2-dithiole-3-thiones are oxidized with nitric acid, decomposition rather than dithiolium formation occurs.

5 Claims, No Drawings

PREPARATION OF DITHIOLIUM COMPOUNDS

Ser. No. 79,709 filed October 9, 1970, now abandoned, describes the preparation of 1,2-dithiolium compounds by oxidizing 1,2-dithiole-3-thiones according to the following equation:

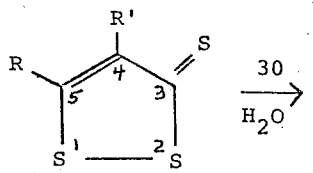

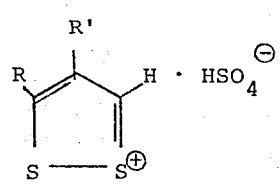

Ser. No. 79,709 further stated as follows:

"A wide variety of oxidizing agents can be employed, as illustrated by the following:

"1. aqueous solution of hydrogen peroxide
"2. hydrogen peroxide and an organic or inorganic acid
"3. barium permanganate
"4. t-butyl-hydroperoxide
"5. m-chloroperbenzoic acid
"6. Caro's acid
"7. peracetic acid
"8. potassium persulfate
"9. chromic anhydride
"10. perchloric acid, etc.
"11. other oxidation agents can also be employed."

The specific oxidizing agents employed in he examples are as follows:
hydrogen peroxide
perchloric acid
m-chloroperberbenzoic acid We have discovered that when nitric acid is employed as an oxidizing agent, as a general rule, the 1,2-dithiole-3-thione decomposes instead of forming the 1,2-dithiolium compound.

However, we have also discovered that when certain sterically hindered 1,2-dithiole-3-thiones are oxidized with nitric acid, the corresponding 1,2-dithiolium compound is formed.

For example, we have discovered that when compounds of the formula

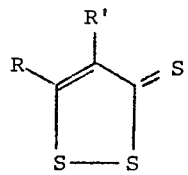

where the R's are tertiary groups, are oxidized, the corresponding 1,2-thiolium compounds are formed.

Thus when 4-neopentyl-5-tert-butyl-1,2-dithiole-3-thione is oxidized with nitric acid 4-neopentyl-5-tertiary-butyl-1,2-dithiolium hydrogen sulfate is formed according to the following equation:

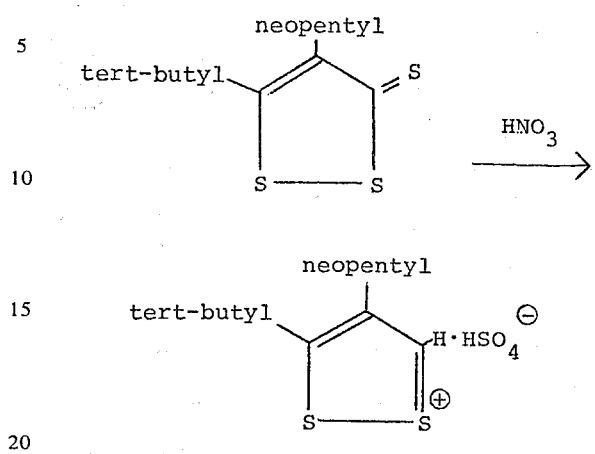

The oxidation is carried out by employing nitric acid at any suitable concentration such as from about 1 to 100% nitric acid. In practice commercially concentrated nitric acid is employed.

Any suitable temperature can be employed so as to minimize side reactions such as from about room temperature to the boiling point of nitric acid which is 86°C., for example from about 40° to 86°C., but preferably from about 60° to 80°C.

The reaction is carried out for a period from about 10 to 600 minutes, for example from about 20 to 300 minutes, but preferably from about 30 to 150 minutes. In practice the reaction is carried out until completion or until the reaction will no longer proceed any further.

The sterically hindered groups are groups stable to oxidation or nitration such as branched aliphatic groups, preferably alkyl, such as tertiary or neopentyl-type groups, having from about 4 to 10,000 carbons, such as from about 4 to 1,000 carbons, for example from about 4 to 100 carbons, but preferably from about 4 to 12 carbons.

Other examples of sterically hindered 1,2-dithiole-3-thiones are those of the polyisobutylene type where the branched alkyl has the general formula

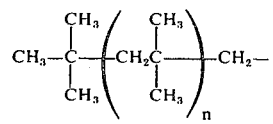

where $n$ is about 1-100, but preferably 1-10.

Ser. No. 79,709 filed October 9, 1970, now abandoned, is hereby incorporated into this application as if part hereof.

The 1,2-dithiolium compounds of this invention can be converted to any of the derivatives described in Ser. No. 79,709. In addition, they can be employed in any of the uses described in Ser. No. 79,709, such as corrosion inhibitors in aqueous and an aerated and/or acidic systems.

The following examples are presented by way of illustration and not of limitation.

EXAMPLE 1

To a reaction flask containing 79g of 70% $HNO_3$ was added, with stirring, 51g of 4-neopentyl-5-tert-butyl- 1,2-dithiole-3-thione at such a rate that reaction temperature of 66-70°C. was maintained (1 hour). After the addition was completed, the mixture was heated for 1½hrs. at 74°-75°C.

The aqueous solution was evaporated under diminished pressure to yield 51.5g (80% of theory) of 4-neopentyl-5-tert-butyl-1,2-dithiolium hydrogen sulfate, m.p. 189-190°C.

Anal. Calc'd for $C_{12}, H_{22}, O_4, S_3$: C, 44.14 H, 6.74 S, 29.43 found; c, 43.98 H, 6.82 S, 29.80

The reaction can be carried out in solvents which do not react with nitric acid, such as acetic acid, as illustrated by the following example.

EXAMPLE 2

To a mixture of 50g of 70% nitric acid and 50g of acetic acid was added, with stirring, 32g of 4-neopentyl-5-t-butyl-1,2-dithiole-3-thione, over a 1 hr. period at such a rate that a reaction temperature of 70°–80°C. was maintained. The mixture was cooled to ambient temperature and the solution evaporated under diminished pressure. The resulting solid was washed with acetone to yield 32g of 4-neopentyl-5-t-butyl 1,2 dithiolium hydrogen sulfate, identical in all respects to the product isolated in example 1.

We claim:

1. A process of oxidizing a sterically hindered 1,2-dithiole-3-thione containing branched aliphatic groups in the 4 and 5 positions to the corresponding 1,2-dithiolium hydrogen sulfate which comprises reacting said sterically hindered 1,2-dithiole-3-thione with nitric acid at a temperature between about 40°C. to about 86°C.

2. The process of claim 1 where the sterically hindered 1,2-dithiole-3-thione is substituted in the 4 and 5 positions with branched aliphatic groups having 4 to 10,000 carbon atoms.

3. The process of claim 2 where the branched aliphatic group contains a tertiary alkyl group.

4. The process of claim 3 where the tertiary alkyl group is tertiary butyl, neopentyl or polyisobutylene.

5. The process of claim 4 where the sterically hindered 1,2-dithiole-3-thione is 4-neopentyl-5-tert-butyl-1,2-dithiole-3-thione.

* * * * *